United States Patent
Yoshida et al.

[11] Patent Number: 6,107,505
[45] Date of Patent: Aug. 22, 2000

[54] PROCESS FOR PRODUCTION OF POLYORGANOSILOXANE

[75] Inventors: Kazuhiro Yoshida; Koichi Ayama, both of Kumamoto; Nobumasa Ootake, Kanagawa, all of Japan

[73] Assignee: Chisso Corporation, Osaka, Japan

[21] Appl. No.: 09/203,401

[22] Filed: Dec. 2, 1998

[30] Foreign Application Priority Data

Dec. 26, 1997 [JP] Japan .................................. 9-368628

[51] Int. Cl.⁷ ...................................................... C07F 7/08
[52] U.S. Cl. ........................ 556/450; 556/440; 556/455; 528/20
[58] Field of Search .................................. 556/450, 455, 556/440; 528/20

[56] References Cited

FOREIGN PATENT DOCUMENTS 8-157605   6/1996   Japan .

OTHER PUBLICATIONS

Noll, "Chemistry and Technology of Silicones", Apr. 1968, Academic Press, Inc.(N.Y.), pp. 191–194.

*Primary Examiner*—Paul F. Shaver
*Attorney, Agent, or Firm*—Oblon, Spivak, McClelland, Maier & Neustadt, P.C.

[57] ABSTRACT

The present invention discloses a process for producing a polyorganosiloxane, which comprises adding an organochlorosilane to a uniform mixture comprising water and at least one kind of alcohol, to subject the organochlorosilane to a hydrolysis and condensation reaction. The organochlorosilane is preferably one represented by the following formula (1):

$$R^1\text{—Si(Cl)}_3 \qquad (1)$$

wherein $R^1$ is a $C_{1-30}$ straight chain saturated or unsaturated hydrocarbon group, a $C_{1-30}$ branched chain saturated or unsaturated hydrocarbon group, a phenyl group, a cyclohexyl group, a $C_{3-15}$ halogenated hydrocarbon group, an acryloxypropyl group or a methacryloxypropyl group.

5 Claims, No Drawings

PROCESS FOR PRODUCTION OF POLYORGANOSILOXANE

BACKGROUND OF THE INVENTION

1. Field of the Invention

The present invention relates to a process for producing a polyorganosiloxane having structural units such as polysilsesquioxane and the like, suitably used as a polymer modifier.

2. Description of the Related Art

Polyorganosiloxanes having a polysilsesquioxane as main structural units have high mechanical properties, heat resistance and electrical insulation, and are therefore in wide use as a protective film in electronic parts and semiconductors, a material for interlayer insulation, a photosensitive material and a material for coating.

Polyorganosiloxanes are produced generally by a process which comprises subjecting at least one kind of organochlorosilane or organoalkoxysilane to a hydrolysis and condensation reaction. Since organoalkoxysilanes are produced from organochlorosilanes, it is obvious that use of an organochlorosilane(s) as a material(s) for production of polyorganosiloxane can produce a polyorganosiloxane at a lower cost.

Many techniques have been reported for production of a polyorganosiloxane from an organochlorosilane(s), and an introductory article on such techniques is given in Chem. Rev. 95, pp. 1409–1430 (1995) by R. H. Baney et al. In this introductory article, it is described that polyphenylsiloxanes having an average molecular weight of 10,000 to several tens of thousands were synthesized from phenyltrichlorosilane by, for example, Brown et al. or Adachi et al. Techniques for synthesizing a polymethylsiloxane from methyltrichlorosilane are disclosed in Japanese Patent Publication No. 17214/1985, U.S. Pat. No. 4,399,266, EPO No. 0406811A1, etc., and it is described in these literatures that polymethylsiloxanes having an average molecular weight of 10,000 to several tens of thousands were produced.

Meanwhile, in Japanese Patent Application Laid-Open No. 157605/1996, etc., it is described that in synthesizing a polyorganosiloxane from methyltrichlorosilane or vinyltrichlorosilane and also in synthesizing a polyorganosiloxane by copolymerizing methyltrichlorosilane or vinyltrichlorosilane with other trichlorosilane, gelation takes place easily during the synthesis and, even if the gelation can be avoided, the resulting polyorganosiloxane is very unstable.

Preferably, polyorganosiloxanes having a polysilsesquioxane as main structural units, when used as a resin modifier or as a material for coating, have a low viscosity for easy handling, has a high content of a reactive group (e.g. a silanol or a functional group), and has a low molecular weight for easy dissolution in solvent or for other reasons. Polyorganosiloxanes having a low molecular weight of several thousands are in production in some cases, as described in Japanese Patent Application Laid-Open No. 227321/1991 or Japanese Patent Application Laid-Open No. 157605/1996. In production of such a low-molecular polyorganosiloxane, a two-phase (aqueous phase and organic phase) interface reaction is used. In this reaction, stirring must be made so that the aqueous phase and the organic phase are not disturbed, which imposes an operational restriction. Further, in the reaction, a large amount of a neutralizing agent (an alkali metal carboxylate) is required, resulting in a higher production cost. The reaction has a further problem in that there is a limitation in the mixing ratio of an alkyl group-containing silane compound and an aromatic group-containing silane compound. Therefore, technical improvements are desired.

SUMMARY OF THE INVENTION

The present inventors made an extensive study on a process for producing a polyorganosiloxane of low molecular weight and excellent storage stability by using methyltrichlorosilane or vinyltrichlorosilane as a starting material. As a result, the present inventors found out that the above-mentioned problems of the prior art can be solved by adding said chlorosilane to a uniform mixture of water and an alcohol to conduct a reaction and also that this novel technique can also be applied not only to other chlorosilanes but also to a single chlorosilane or a mixture of two or more different chlorosilanes. The present invention has been completed based on the above finding.

Hence, the object of the present invention is to provide a process for producing a polyorganosiloxane of low molecular weight and excellent storage stability at a high yield at a low cost without causing gelation, by subjecting to hydrolysis and condensation at least one kind of organochlorosilane, particularly organotrichlorosilane.

The present invention lies in a process for producing a polyorganosiloxane, which comprises adding an organochlorosilane to a uniform mixture comprising water and at least one kind of alcohol, to subject the organochlorosilane to a hydrolysis and condensation reaction.

The present invention also lies in a process for producing a polyorganosiloxane, which comprises dropping methyltrichlorosilane at a temperature ranging from −30 to 35° C. to a uniform mixture comprising water and an alcohol, the amount of water in the mixture being 1–3 times the stoichiometric amount of water needed for complete hydrolysis of the three —Cl groups bonding to the silicon atom of methyltrichlorosilane and the amount of the alcohol in the mixture being 1–30 times the volume of methyltrichlorosilane, to subject the methyltrichlorosilane to a hydrolysis and condensation reaction.

According to the process of the present invention, a polyorganosiloxane of narrow molecular weight distribution, low average molecular weight and excellent storage stability can be produced without causing gelation or the like.

In the hydrolysis and condensation reaction of organochlorosilane, the raw materials may consist of only an organochlorosilane, an alcohol and water. Even in this case, there can be produced, at a low cost, a polyorganosiloxane which can be suitably used as a resin modifier or as a material for coating.

DETAILED DESCRIPTION OF THE PREFERRED EMBODIMENTS

The present invention is characterized in that an organochlorosilane is added to a uniform mixture comprising an alcohol and a desired concentration of water, to give rise to a hydrolysis and condensation reaction.

In the process of the present invention, there are preferably used, as the organochlorosilane, organotrichlorosilanes represented by the following formula (1), organodichlorosilanes represented by the following formula (2), organomonochlorosilanes represented by the following formula (3), organotetrachlorosilanes, etc.

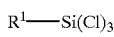

(1)

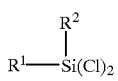

(2)

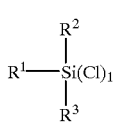

(3)

wherein $R^1$, $R^2$ and $R^3$ are each independently a $C_{1-30}$ straight chain saturated hydrocarbon group, a $C_{2-30}$ straight chain unsaturated hydrocarbon group, a $C_{3-30}$ branched chain saturated or unsaturated hydrocarbon group, a phenyl group, a cyclohexyl group, a $C_{3-15}$ halogenated hydrocarbon group, an acryloxypropyl group or a methacryloxypropyl group.

As the hydrocarbon group, a $C_{1-18}$ hydrocarbon group is particularly preferred for the availability reason and a $C_{1-6}$ hydrocarbon group is more preferred. The halogenated hydrocarbon group can be exemplified by chloropropyl, trichloropropyl, (perfluoro-n-butyl)ethyl, (perfluoro-n-hexyl)ethyl and (perfluoro-n-dodecyl)ethyl.

Specific examples of the organotrichlorosilane are methyltrichlorosilane, ethyltrichlorosilane, n-propyltrichlorosilane, n-butyltrichlorosilane, i-butyltrichlorosilane, t-butyltrichlorosilane, pentyltrichlorosilane, hexyltrichlorosilane, n-heptyltrichlorosilane, n-octyltrichlorosilane, i-octyltrichlorosilane, nonyltrichlorosilane, n-decyltrichlorosilane, vinyltrichlorosilane, allyltrichlorosilane, phenyltrichlorosilane, benzyltrichlorosilane, cyclohexyltrichlorosilane, (3-acryloxypropyl)trichlorosilane, methacryloxypropyl-trichlorosilane and 3-chloropropyltrichlorosilane.

As mentioned above, the organotrichlorosilane may as necessary be mixed with an organodichlorosilane or an organomonochlorosilane. When an organodichlorosilane or an organomonochlorosilane is used as, for example, a terminator, the addition amount is appropriately determined depending upon the chemical structure, molecular weight, etc. of the polyorganosiloxane produced. The addition amount per se is known to those skilled in the art.

The organodichlorosilane can be exemplified by dimethyldichlorosilane, diethyldichlorosilane, diisopropyldichlorosilane, di-n-butyldichlorosilane, divinyldichlorosilane, diallyldichlorosilane, diphenyldichlorosilane and dicyclohexyldichlorosilane.

The organomonochlorosilane can be exemplified by trimethylchlorosilane, triethylchlorosilane, tri-n-propylchlorosilane, tri-n-butylchlorosilane, trivinylchlorosilane, triphenylchlorosilane and tribenzylchlorosilane.

In the present process, there is used, as the organochlorosilane, particularly an organotrichlorisilane represented by the formula (1) singly or as the main component; as necessary, an organomonochlorosilane, an organodichlorosilane, a tetrachlorosilane, etc. are added appropriately and a hydrolysis and condensation reaction is allowed to take place; thereby, a polysilsesquioxane can be produced. This polysilsesquioxane compound is industrially useful as a protective film or a material for coating.

In the present process, an organochlorosilane is added to a uniform mixture comprising an alcohol and a required amount of water.

In the present process, the uniform mixture of water and an alcohol must be a complete solution of water and an alcohol. In the present process, no nonuniform mixture is usable in which either of water and an alcohol is present in excess, they are unable to form a complete solution and two phases are present. A nonuniform mixture consisting of two phases is seen at times when propyl alcohol or a higher alcohol is used. When a nonuniform mixture is used in production of polyorganosiloxane, there is no reproducibility in the molecular weight of the polyorganosiloxane produced and, moreover, gelation tends to occur.

There is no particular restriction as to the method for adding the organochlorosilane to the uniform mixture; however, it is preferred to add the organochlorosilane to the uniform mixture slowly in small portions in a relatively long period of time and it is not preferred to add the organochlorosilane to the uniform mixture in a short period of time. By employing such an addition method can be obtained a polyorganosiloxane having a low average molecular weight, a narrow molecular weight distribution and excellent storage stability. Specific addition methods include dropping or successive injection in small portions. Stirring is preferably conducted during the addition of the organochlorosilane.

The alcohol used is a straight chain or branched chain alcohol whose carbon atoms are preferably 1 to 4. Specific examples of the alcohol are methyl alcohol, ethyl alcohol, n-propyl alcohol, i-propyl alcohol, n-butyl alcohol, i-butyl alcohol and t-butyl alcohol. An alcohol having 1 to 3 carbon atoms is most preferred for its high compatibility with water.

An alcohol having 5 or more carbon atoms may be used. Such an alcohol, however, has low solubility in water, which may make it difficult to form a uniform water-alcohol mixture. When an alcohol having 5 or more carbon atoms is used, it may be difficult to control the molecular weight of the polyorganosiloxane formed, at high reproducibility.

The amount of the alcohol in the uniform mixture is preferably 1–30 times, more preferably 2–8 times (by volume) the amount of the organochlorosilane added.

When the amount of the alcohol used is less than 1 time (by volume) the amount of the organochlorosilane added, the polyorganosiloxane produced tends to cause gelation. When the amount of the alcohol used is more than 30 times (by volume) the amount of the organochlorosilane added, there is no particular problem; however, use of the alcohol in such a large amount is uneconomical.

The amount of water in the uniform mixture is preferably 0.5–30 times the stoichiometric amount of water needed for hydrolysis of the total chlorine (—Cl) groups bonding to the silicon atom of organotrichlorosilane.

The stoichiometric amount of water needed for hydrolysis of the total —Cl groups of, for example, the organotrichlorosilane represented by the formula (1) can be calculated according to the following reaction formula (A). In the following, a formula (4) refers to a polyorganosiloxane.

(A)

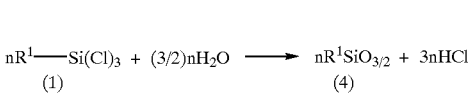

There is no particular restriction as to the amount of water added to the alcohol, i.e. the amount of water in the uniform mixture, because even if water is added in an amount slightly smaller than the stoichiometric amount of water needed for hydrolysis of the total —Cl groups bonding to the silicon atom of organochlorosilane, hydrolysis is completely conducted in the next step of water washing described later. When the amount of water added to the alcohol is extremely small, the organochlorosilane is not sufficiently hydrolyzed in the reaction step and, in this state, water-washing is conducted; as a result, the polyorganosiloxane obtained has a wide molecular weight distribution and has no stable quality.

There is no particular restriction as to the upper limit of the amount of water in the uniform mixture. When the amount of water is too large, however, there arise problems, for example, (1) the production efficiency of polyorganosiloxane is low and (2) when an alcohol of high molecular weight is used as a solvent, water is not completely dissolved therein and phase separation is invited, making it impossible to produce a polyorganosiloxane of stable quality. Hence, the amount of water added is preferably about 0.5 to 30 times, more preferably 1 to 20 times the stoichiometric amount of water needed for hydrolysis of the total —Cl groups bonding to the silicon atom of organochlorosilane.

It was found out that when a trichlorosilane $R^1Si(Cl)_3$ is used and the molecular weight of $R^1$ is lower, a polyorganosiloxane having a higher molecular weight is obtained when the amount of water added is large and that when $R^1$ is a methyl group, gelation occurs when the amount of water added exceeds a certain level. Therefore, when $R^1$ is a methyl group, the amount of water added to the alcohol is preferably 1–3 times, particularly preferably 1–2 times the stoichiometric amount of water needed for complete hydrolysis of the three —Cl groups bonding to the silicon atom of methyltrichlorosilane.

Hydrochloric acid is generated in the hydrolysis and condensation reaction of organochlorosilane. However, when water-washing is conducted in a post-treatment, it is not necessary to neutralize this hydrochloric acid with a neutralizing agent in the reaction because hydrochloric acid can be easily and surely removed in the post-treatment. No neutralizing agent is necessary even in the water-washing (post-treatment). A neutralizing agent may be used in the water-washing but is not preferred for a lower production cost.

The neutralizing agent (which may be used) can be exemplified by the following bases: alkali metal hydroxides such as lithium hydroxide, sodium hydroxide, potassium hydroxide and the like; alkaline earth metal hydroxides such as calcium hydroxide, barium hydroxide and the like; alkali metal carbonates such as sodium carbonate, potassium carbonate and the like; amines such as dimethylamine, diethylamine, triethylamine and the like; organic amines such as pyridine and the like; and ammonia.

In using a neutralizing agent, it is to be noted that when the organochlorosilane is methyltrichlorosilane [a $R^1$—Si$(Cl)_3$ wherein $R^1$ is a methyl group], use of neutralizing agent either in the reaction or in the water-washing gives a product of high molecular weight or causes gelation. Therefore, use of neutralizing agent is not preferred particularly when a polymethylsiloxane is produced from methyltrichlorosilane according to the present invention.

As mentioned above, an organochlorosilane is subjected to hydrolysis and condensation in the present process. The starting materials used are at least an organochlorosilane, an alcohol and water. By simply conducting hydrolysis and condensation using only these starting materials, a polyorganosiloxane having a narrow molecular weight distribution, a low average molecular weight and excellent storage stability can be obtained. The reaction proceeds efficiently without using any substance (starting material, additive or neutralizing agent) other than the above starting materials.

A neutralizing agent and/or an organic solvent other than alcohol may be used as necessary. As mentioned above, when a neutralizing agent is used, it is desirably when $R^1$ of $R^1$—Si$(Cl)_3$ is a group other than methyl group. When an organic solvent is used in combination with an alcohol, an alcohol/organic combination is selected in which the alcohol and the organic solvent can form a uniform mixture with water.

The reaction time differs depending upon the reaction temperature and kind of organochlorosilane used, but the reaction is complete in a relatively short period of time.

In the present process, it is preferred to wash the reaction mixture obtained in the hydrolysis and condensation reaction, with water in a post-operation. This operation is conducted to remove the hydrochloric acid generated in the hydrolysis and condensation reaction, from the reaction mixture. The water-washing is conducted several times until the reaction mixture becomes neutral. Water of 0.3 to 5 times the amount of the reaction mixture is used ordinarily. The times of water-washing are about 4. By this operation, the reaction mixture is made nearly neutral. When in the water-washing, an emulsion is formed and phase separation of water from the product is difficult, an organic solvent (e.g. tetrahydrofuran, toluene, hexane or isopropyl alcohol) or sodium chloride is added so that the phase separation can be easily conducted.

The hydrolysis temperature is preferably –40 to 120° C., particularly preferably –30 to 80° C. When the reaction temperature is higher than 120° C., the polyorganosiloxane formed may have a high molecular weight or gelation may take place. When the hydrolysis temperature is lower than –40° C., the hydrolysis does not proceed sufficiently. When $R^1$ of $R^1$—Si$(Cl)_3$ is a methyl group, the above phenomena appear more strikingly. Therefore, the hydrolysis and condensation temperature of methyltrichlorosilane is preferably –30 to 35° C.

The reaction mixture after the water-washing is then subjected as necessary to known treatments ordinarily employed, such as drying, solvent distillation, purification and the like, whereby a polyorganosiloxane (an intended compound) can be obtained.

The present invention is described specifically below by way of Examples. However, the present invention is not restricted to these Examples.

EXAMPLE 1

Production of polyorganosiloxane from methyltrichlorosilane

Hydrolysis and Condensation Reaction

Into a 200-ml four-necked flask equipped with a thermometer, a reflux condenser, a dropping funnel and a stirrer were fed 50 g of i-propyl alcohol and 3.6 g of pure water (3.6 g was 1.0 time the stoichiometric amount of water needed for hydrolysis of the total —Cl groups in 0.20 mole of methyltrichlorosilane). The mixture was cooled on an ice bath and the temperature of the flask contents was kept at 0 to 8° C. Thereto was dropwise added 20 g (0.13 mole) of methyltrichlorosilane in 90 minutes. The resulting mixture was stirred for 3 hours with the above temperature being kept.

Water-Washing

To the reaction mixture obtained were added 50 g of toluene and 30 g of pure water, followed by stirring. The flask contents were transferred into a separatory funnel and allowed to stand. Then, the resulting water layer was removed. The organic layer was washed four times each with 100 g of pure water (the washings became neutral). The organic layer after water-washing was filtered and then subjected to distillation at 60° C. under reduced pressure by the use of an evaporator to remove the solvent, water, etc. in the organic layer, whereby 8.3 g of a colorless and transparent polymethylsiloxane was obtained.

This polymethylsiloxane was soluble in toluene, tetrahydrofuran and chloroform. It had an Mn of 980, an Mw of 1,230 (on a polystyrene-reduced base) and an Mw/Mn of 1.25 as measured by gel permeation chromatography (GPC).

EXAMPLE 2

Production of polyorganosiloxane from methyltrichlorosilane

Into the same apparatus as used in Example 1 were fed 50 g of i-propyl alcohol and 3.6 g of pure water. The mixture was cooled on an ice bath and the temperature of the flask contents was kept at 20 to 28° C. Thereto was dropwise added 20 g of methyltrichlorosilane in 25 minutes. The resulting mixture was stirred for 3 hours at room temperature.

The resulting reaction mixture was subjected to the same water-washing and post-treatment as conducted in Example 1, to obtain 9.3 g of a polymethylsiloxane. It had an Mn of 1,210, an Mw of 1,910 and an Mw/Mn of 1.58 as measured by GPC.

EXAMPLE 3

Production of polyorganosiloxane from methyltrichlorosilane

Into the same apparatus as used in Example 1 were fed 50 g of methyl alcohol and 3.6 g of pure water. The mixture was cooled on an ice bath and the temperature of the flask contents was kept at 0 to 8° C. Thereto was dropwise added 20 g of methyltrichlorosilane in 80 minutes. The resulting mixture was stirred for 3 hours at 0° C.

The resulting reaction mixture was subjected to the same water-washing and post-treatment as conducted in Example 1, to obtain 7.8 g of a polymethylsiloxane. It had an Mn of 1,020, an Mw of 1,340 and an Mw/Mn of 1.32 as measured by GPC.

EXAMPLE 4

Production of polyorganosiloxane from methyltrichlorosilane

Into the same apparatus as used in Example 1 were fed 50 g of i-butyl alcohol and 3.6 g of pure water. The mixture was cooled on an ice bath and the temperature of the flask contents was kept at 0 to 8° C. Thereto was dropwise added 20 g of methyltrichlorosilane in 120 minutes. The resulting mixture was stirred for 3 hours at 0° C.

The resulting reaction mixture was subjected to the same water-washing and post-treatment as conducted in Example 1, to obtain 7.7 g of a polymethylsiloxane. It had an Mn of 1,670, an Mw of 3,460 and an Mw/Mn of 2.08 as measured by GPC.

EXAMPLE 5

Production of polyorganosiloxane from ethyltrichlorosilane 11.0 g of a polyethylsiloxane was obtained according to the same procedure as employed in Example 1, by using 20 g of ethyltrichlorosilane, 3.3 g of pure water (3.3 g was 1.0 time the stoichiometric amount of water needed for hydrolysis of the total —Cl groups in ethyltrichlorosilane) and 50 g of i-propyl alcohol. The polyethylsiloxane had an Mn of 680, an Mw of 730 and an Mw/Mn of 1.08 as measured by GPC.

EXAMPLE 6

Production of polyorganosiloxane from ethyltrichlorosilane

Into the same apparatus as used in Example 1 were fed 50 g of i-propyl alcohol and 22 g of pure water (22 g (1.2 mol)was 6.8 times the stoichiometric amount of water needed for hydrolysis of the total —Cl groups in 0.12 moles of ethyltrichlorosilane). The mixture was cooled on an ice bath and the temperature of the flask contents was kept at 5 to 25° C. Thereto was dropwise added 20 g (0.12 mole) of ethyltrichlorosilane in 30 minutes. The resulting mixture was stirred for 3 hours with the temperature being kept at 5° C.

To the reaction mixture obtained were added 50 g of toluene and 30 g of pure water, followed by stirring. The flask contents were transferred into a separatory funnel and allowed to stand. Then, the resulting water layer was removed. The organic layer was washed with a 4% (by weight) aqueous sodium hydroxide solution to neutralize the hydrogen chloride generated in the hydrolysis, followed by removal of the resulting aqueous layer. The organic layer was washed three times each with 30 g of pure water (the washings became neutral). The organic layer after water-washing was filtered and then subjected to distillation at 60° C. under reduced pressure by the use of an evaporator to remove the solvent, water, etc. in the organic layer, whereby 9.8 g of a colorless and transparent polyethylsiloxane was obtained. This polyethylsiloxane had an Mn of 1,150, an Mw of 2,040 and an Mw/Mn of 1.78 as measured by GPC.

EXAMPLE 7

Production of polyorganosiloxane from ethyltrichlorosilane

Into the same apparatus as used in Example 1 were fed 22 g of pure water and 50 g of methyl alcohol. Thereto was dropwise added 20 g of ethyltrichlorosilane in 15 minutes with stirring at room temperature. The temperature of the flask contents increased to 70° C. After the completion of the dropwise addition, the mixture was stirred for 1 hour at room temperature and then subjected to an additional 2-hour reaction at 78° C. Thereafter, the temperature was dropped to room temperature.

The resulting reaction mixture was subjected to the same water-washing and post-treatment as conducted in Example 6, to obtain 10.3 g of a polyethylsiloxane. This polyethylsiloxane had an Mn of 1,160, an Mw of 2,250 and an Mw/Mn of 1.94 as measured by GPC.

EXAMPLE 8

Production of polyorganosiloxane from vinyltrichlorosilane 9.6 g of a polyvinylsiloxane was obtained according to the same procedure as employed in Example 1, by using 20 g of vinyltrichlorosilane, 3.6 g of pure water (3.6 g was 1.0 time the stoichiometric amount of water needed for hydrolysis of the total —Cl groups in vinyltrichlorosilane) and 50 g of i-propyl alcohol. The polyvinylsiloxane had an Mn of 790, an Mw of 900 and an Mw/Mn of 1.14 as measured by GPC.

EXAMPLE 9

Production of polyorganosiloxane from vinyltrichlorosilane 9.4 g of a polyvinylsiloxane was obtained according to the same procedure as employed in Example 1, by using 20 g of vinyltrichlorosilane, 22.0 g of pure water (22.0 g was 6.4 times the stoichiometric amount of water needed for hydrolysis of the total —Cl groups in vinyltrichlorosilane) and 50 g of i-propyl alcohol. The polyvinylsiloxane had an Mn of 1,200, an Mw of 3,690 and an Mw/Mn of 3.07 as measured by GPC.

EXAMPLE 10

Production of polyorganosiloxane from methacryloxypropyltrichlorosilane 12.7 g of a polymethacryloxypropylsiloxane was obtained according to the same procedure as employed in Example 1, by using 20 g of methacryloxypropyltrichlorosilane, 2.1 g of pure water (2.1 g was 1.0 time the stoichiometric amount of water needed for hydrolysis of the total —Cl groups in methacryloxypropyltrichlorosilane) and 50 g of i-propyl alcohol. The polymethacryloxypropylsiloxane had an Mn of 870, an Mw of 920 and an Mw/Mn of 1.05 as measured by GPC.

EXAMPLE 11

Production of polyorganosiloxane from n-propyltrichlorosilane 12.8 g of a poly(n-propyl)siloxane was obtained according to the same procedure as employed in Example 1, by using 20 g of n-propyltrichlorosilane, 3.1 g of pure water (3.1 g was 1.0 time the stoichiometric amount of water needed for hydrolysis of the total —Cl groups in n-propyltrichlorosilane) and 50 g of i-propyl alcohol. The poly(n-propyl)siloxane had an Mn of 750, an Mw of 800 and an Mw/Mn of 1.07 as measured by GPC.

EXAMPLE 12

Production of polyorganosiloxane from methyltrichlorosilane and methacryloxypropyltrichlorosilane 9.3 g of a polymethyl(methacryloxypropyl)siloxane was obtained according to the same procedure as employed in Example 1, by using 14.9 g of methyltrichlorosilane, 5.2 g of methacryloxypropyltrichlorosilane, 3.2 g of pure water (3.2 g was 1.0 time the stoichiometric amount of water needed for hydrolysis of the total —Cl groups in the two trichlorosilanes) and 50 g of i-propyl alcohol. The polymethyl(methacryloxypropyl)siloxane had an Mn of 950, an Mw of 1,100 and an Mw/Mn of 1.16 as measured by GPC.

EXAMPLE 13

Production of polyorganosiloxane from n-propyltrichlorosilane

Hydrolysis and Condensation Reaction

Into a 200-ml four-necked flask equipped with a thermometer, a reflux condenser, a dropping funnel and a stirrer were fed 100 g (126 ml) of methyl alcohol (sp.gr.: 0.791) and 40 g of pure water (40 g was 2.0 times the stoichiometric amount of water needed for hydrolysis of the total —Cl groups in 130 g of n-propyltrichlorosilane). The mixture was cooled on an ice bath and the temperature of the flask contents was kept at 0 to 8° C. Thereto was dropwise added 130 g (110 ml) of n-propyltrichlorosilane (sp. gr.: 1.185) in 90 minutes. The resulting mixture was stirred for 3 hours with the above temperature being kept.

Water-Washing

To the reaction mixture obtained were added 50 g of toluene and 30 g of pure water, followed by stirring. The flask contents were transferred into a separatory funnel and allowed to stand. Then, the resulting water layer was removed. 30 g of isopropyl alcohol and 100 g of pure water were added into the separatory funnel to wash the organic layer with water. The organic layer was further washed four times each with 100 g of pure water (the washings became neutral). The organic layer after water-washing was filtered and then subjected to distillation at 60° C. under reduced pressure by the use of an evaporator to remove the solvent, water, etc. in the organic layer, whereby 83 g of a colorless and transparent polypropylsiloxane was obtained.

This polypropylsiloxane was soluble in toluene, tetrahydrofuran and chloroform. It had an Mn of 1,260, an Mw of 1,530 (on a standard polystyrene-reduced base) and an Mw/Mn of 1.21 as measured by gel permeation chromatography (GPC).

Incidentally, the volume ratio of methyl alcohol and n-propyltrichlorosilane was 1.15.

TEST EXAMPLE 1

Storage Stability Test

The polymethylsiloxane produced in Example 2 was diluted with tetrahydrofuran to make a 25% (by weight) solution. The solution was placed in a thermostat of 40° C. for 120 hours, whereby a storage stability test was conducted. As shown in Table 1, there was no change in average molecular weight or in molecular weight distribution. Thus, the polymethylsiloxane produced according to the present invention process had high storage stability.

TABLE 1

| Time (hr) | Mn | Mw | Mw/Mn |
| --- | --- | --- | --- |
| 0 | 1210 | 3190 | 1.52 |
| 24 | 1250 | 3440 | 1.55 |
| 120 | 1220 | 3440 | 1.58 |

TEST EXAMPLE 2

A hydrolysis and condensation reaction was conducted in the same manner as in Example 1, by using 20 g of methyltrichlorosilane, 3.6 g of pure water and 50 g of i-propyl alcohol. The reaction mixture was transferred into a separatory funnel to remove the water layer. To the organic layer was added a 4% (by weight) aqueous sodium hydroxide solution to conduct neutralization. A gel formed.

COMPARATIVE EXAMPLE 1

An operation was conducted in the same manner as in Example 1 except that 50 g of i-propyl alcohol was replaced by 50 g of tetrahydrofuran (THF). The polymethylsiloxane obtained was gel-like.

COMPARATIVE EXAMPLE 2

An operation was conducted in the same manner as in Example 1 except that 50 g of i-propyl alcohol was replaced by 50 g of acetone. The polymethylsiloxane obtained was gel-like.

COMPARATIVE EXAMPLE 3

An operation was conducted in the same manner as in Example 1 except that pure water was used in an amount of 24 g (which was 3.4 times the stoichiometric amount of water needed for hydrolysis of the total —Cl groups in 1 mole of methyltrichlorosilane). The polymethylsiloxane obtained was gel-like.

COMPARATIVE EXAMPLE 4

The same operation as in Example 1 was conducted using 130 g (110 ml) of n-propyltrichlorosilane (sp. gr.: 1.185), 100 g (124.5 ml) of isobutyl alcohol (sp. gr.: 0.803) and 40 g of pure water (40 g was 2.0 times the stoichiometric amount of water needed for hydrolysis of the total —Cl groups in 130 g of n-propyltrichlorosilane).

The mixture of 100 g of isobutyl alcohol and 40 g of pure water was not a complete solution but a cloudy and translucent suspension.

After the completion of the reaction, there was a large amount of gel adhering to the inside wall of the flask. The poly(n-propylsiloxane) yield was low at 62 g. GPC gave Mn=2,180, Mw=4,900 and Mw/Mn=2.25.

Incidentally, the volume ratio of isobutyl alcohol and n-propyltrichlorosilane was 1.13.

COMPARATIVE EXAMPLE 5

The same operation as in Comparative Example 4 was repeated. The poly(n-propylsiloxane) yield was 73 g. GPC gave Mn=1,660, Mw=2,110 and Mw/Mn=1.27, and the reproducibility of hydrolysis and condensation reaction was inferior.

The reason for inferior reproducibity is presumed to be due to the translucent nonuniform mixture between 100 g of isobutyl alcohol and 40 g of pure water. The nonuniform mixture consisted of two phases (water was suspended in isobutyl aochol). It is presumed that the suspension state of the two-phase mixture changed subtly depending upon the condition of stirring and the hydrolysis and condensation reaction of n-propyltrichlorosilane was affected by the change of the suspension state of water and isobutyl alcohol. That is, the hydrolysis and condensation reaction in this two-phase mixture is inferior in reproducibility.

What is claimed is:

1. A process for producing a polyorganosiloxane, which comprises adding an organochlorosilane represented by the following formula (1):

$$R^1\text{—Si(Cl)}_3 \qquad (1)$$

wherein $R^1$ is a $C_{2-30}$ straight chain saturated or unsaturated hydrocarbon group, a $C_{3-30}$ branched chain saturated or unsaturated hydrocarbon group, a phenyl group, a cyclohexyl group, a $C_{3-15}$ halogenated hydrocarbon group, an acryloxypropyl group or a methacryloxypropyl group, to a uniform mixture comprising water and at least one kind of $C_{1-3}$ straight chain or branched alcohol, to subject the organochlorosilane to a hydrolysis and condensation reaction, wherein the amount of the alcohol in the uniform mixture is 1–30 times (by volume) the amount of organochlorosilane, and the amount of water in the uniform mixture comprising water and an alcohol is 1–30 times the stoichiometric amount of water needed for hydrolysis of the total —Cl groups in organotrichlorosilane.

2. A process according to claim 1, wherein the organochlorosilane is methyltrichlorosilane and the amount of water in the uniform mixture comprising water and an alcohol is 1–3 times the stoichiometric amount of water needed for hydrolysis of the total —Cl groups in methyltrichlorosilane.

3. A process according to claim 1, wherein after the completion of the hydrolysis and condensation reaction, the reaction mixture is washed with water to remove the hydrochloric acid formed by the reaction.

4. A process for producing a polyorganosiloxane, which comprises adding methyltrichlorosilane at a temperature ranging from −30 to 35° C. to a uniform mixture comprising water and a $C_{1-3}$ straight chain or branched chain alcohol, the amount of water in the mixture being 1–3 times the stoichiometric amount of water needed for complete hydrolysis of the three —Cl groups bonding to the silicon atom of methyltrichlorosilane and the amount of the alcohol in the mixture being 1–30 times the volume of methyltrichlorosilane, to subject the methyltrichlorosilane to a hydrolysis and condensation reaction.

5. A process according to claim 4, wherein the uniform mixture consists essentially of water and an alcohol.

* * * * *